United States Patent [19]

Lloyd et al.

[11] 4,245,630
[45] Jan. 20, 1981

[54] TEARABLE COMPOSITE STRIP OF MATERIALS

[75] Inventors: Ronald Lloyd, Sawbridgeworth; Brian W. Walter, Bishop's Stortford, both of England

[73] Assignee: T. J. Smith & Nephew, Ltd., Great Britain

[21] Appl. No.: 17,062

[22] Filed: Mar. 2, 1979

Related U.S. Application Data

[63] Continuation of Ser. No. 840,665, Oct. 11, 1977, abandoned.

[30] Foreign Application Priority Data

Oct. 8, 1976 [GB] United Kingdom ............... 42046/76
Aug. 5, 1977 [GB] United Kingdom ............... 32985/77

[51] Int. Cl.³ .......................... B32B 7/06; A61F 13/00
[52] U.S. Cl. ................................. 128/155; 428/43; 428/167; 428/172; 428/189; 428/255; 428/315
[58] Field of Search ................ 428/40, 41, 42, 43, 428/167, 172, 189, 315, 255; 128/155, 156, 290 R, 296; 156/252; 206/440

[56] References Cited

U.S. PATENT DOCUMENTS

| 2,703,083 | 3/1955 | Gross | 128/156 |
| 2,734,503 | 2/1956 | Doyle | 128/156 |
| 3,085,024 | 4/1963 | Blackford | 428/43 |
| 3,143,208 | 8/1964 | Sizemore | 128/155 |

*Primary Examiner*—Paul J. Thibodeau
*Attorney, Agent, or Firm*—Louis E. Marn; Elliot M. Olstein

[57] ABSTRACT

A composite strip material comprising at least a backing layer, an adhesive layer on a surface thereof, and a removable protective layer over and contacting and peelably adherent to at least part of the adhesive layer; wherein each layer is finger-tearable and wherein at least one layer is cleanly finger-tearable from any point along its length in a predetermined transverse direction, thereby to influence and facilitate transverse tear of any other layers present in a like cleanly finger-tearable manner to provide clearly defined separate units of any desired size.

33 Claims, 8 Drawing Figures

TEARABLE COMPOSITE STRIP OF MATERIALS

This application is a continuation of Ser. No. 840,665, filed Oct. 11, 1977, now abandoned.

This invention relates to material in strip form with an adhesive layer occupying the whole or part of one or both surfaces.

Primarily the invention is concerned with surgical dressings or first aid dressings, but it is also concerned with other medical or personal hygiene products and may have wider applicability to adhesive tape products generally such as masking tape or double-sided adhesive tape.

When adhesive-coated strip material is provided in roll form there is sometimes difficulty in separating individual portions for use. Usually these portions are cut off e.g. by using scissors or torn off by pulling over a serated edge which provides perforations. The difficulty of separating individual portions is particularly noticeable with polymer foil substrates since these are commonly longitudinally oriented and thus resist transverse tear.

In the medical field, where the present invention is of primary utility, it is known to provide surgical strapping tape in a roll and cut from this roll of tape covered at one side with adhesive a desired length of material using scissors. This is suitable in a clinic or surgery where the material is constantly in use, but in the home where a dressing is only required occasionally it is felt more to be more convenient and hygienic to provide first aid dressings of various sizes in the form of discrete pieces e.g. in a tin or box.

The present invention provides a composite strip material comprising at least a backing layer, an adhesive layer on a surface thereof, and a removable protective layer over and contacting and peelably adherent to at least part of the adhesive layer; wherein each layer is finger-tearable and wherein at least one layer is cleanly finger-tearable from any point along its length in a predetermined transverse direction, thereby to influence and facilitate such transverse tear of any other layers present in a like cleanly finger-tearable manner to provide clearly defined separate units of any desired size.

Usually, although not necessarily, the material is provided as a folded length; it may alternatively be provided as a roll of material.

The term "cleanly finger-tearable" means that the material can be grasped between finger and thumb on one side of a desired tear line and between the finger and thumb of the other hand on the other side of the desired tear line, and torn in a straight well-defined line giving clear torn edges, by bending the grasped material in opposite directions out of its plane and thereafter continuing this tearing movement. The tearing action is like tearing a sheet of paper.

According to the invention such composite material, provided at least one layer is programmed to provide such tear, tears cleanly across both or all layers into units (such as dressings, pads, labels, adhesive patches) which are substantially larger than any tear-programming and which could indeed be subdivided, by tearing, into a high number of cleanly divided sub-units. It is not to be confused with separating from a roll pre-cut or pre-scored units of predetermined uniform sizes, which are themselves indivisible.

The term "strip" of material covers any longitudinally extending shaped area of material and especially as a sheet which is divisible into elongate portions themselves tearable as described above.

Exact analysis of what happens during tearing a sheet of material is complex. There is a distinction to be drawn between "transverse tear" and "trouser-leg tear". In the former, the sheet is separately clamped in its plane over the whole area to either side of the parting line, and the separate clamps are moved apart. Eventually, the material tears, the force needed depending on whether or not the tear is a propagation of an initial edge-notch. In the latter, a strip of material is torn away from the plane of the remaining material, either with a progressively moving point of application getting farther from the sheet (and hence exerting less control over the line of tear) or with a stationary point of application, e.g. over a roller at the surface of the sheet. Moreover, the magnitude and uniformity of applied forces and separation speeds also affect the outcome.

Finger-tearing of a sheet of material combines elements of transverse tear (in that the two parts of the sheet may be separated relatively to their position on their initial plane, and the actual gripping areas of thumb and finger are not negligible) and "trouser leg" tear, modified in that the position of thumb and finger can change as the tear progresses.

Whatever the reason, we have found that the clean finger-tear across both or all layers is a surprising and novel effect. Moreover, the force required, as described more fully below, is not merely additive of the force required for each separate layer.

In a simple form of the invention both the backing layer and the protective layer are independently cleanly finger-tearable in the predetermined transverse direction as above. However, the invention can also be operated when only one of these layers is tearable in this way provided that this said one layer is dominant, although it may be slightly more difficult to tear the strip in such an instance.

A preferred specific form of the invention relates to such a composite strip tearable into individual medical or surgical dressings consisting essentially of the backing layer with the said adhesive layer on one surface thereof; means defining at least one operative zone at or on the said surface of the backing layer said zone being narrower than and parallel to the edges of the backing layer; and a protective cover layer, at least as wide as the backing layer contacting and peelably adherent to at least part of the adhesive layer.

The operative zone, which may be visible or not apparent to the eye, can for instance be a zone of bactericidal material or other medicament. It could also conceivably be merely an adhesive-free zone. Most preferably, however, it is an absorbent zone, and in particular the, or each zone, may be an elongate tearable pad. Preferably, there is one such pad extending along a generally central zone of the strip as a narrow strip.

Optionally, the pad can be provided with an upper cover layer of for example, a net. The pad can be made of gauze or a foamed polymeric product and we have found that a styrene-butadiene foam rubber layer is useful. Once again, the nature of the pad itself is not of primary importance to the invention, although it should be readily tearable. It is conceivable that the pad could be profiled or perforated to permit generally transverse tear but normally the transverse tear properties will be provided by either the backing layer or the protective layer as described above.

One or both layers should be cleanly finger-tearable, starting at any point along the length, in a predetermined transverse direction. Preferably this is achieved by perforations whether coaxial or not through one or more layers, or by profiling one or both surfaces of one or more layers, or by a combination of both, all as explained in more detail below.

It is known to perforate, for example, at least the backing layer of a surgical dressing, so that it is permeable to air and water vapour and allows the wound to heal more rapidly. It is also known to pigment and profile the back of a dressing, so as to match more closely the surface appearance of the skin. It is moreover known to provide a continuous strip of material with a spaced succession of cuts (e.g. British Pat. No. 536,206) or edge slits (U.S. Pat. No. 2,508,855) to facilitate tearing of predetermined unit portions as thereby defined. However, the present invention, while capable of achieving the advantages of these features, is distinct from all of them. Thus, perforations in or profiling of a dressing have not hitherto been shaped and arranged to facilitate clean finger-tear at any desired point, while detachment of predetermined units means that each strip can only provide one sort of dressing instead of all different sorts as desired.

According to the invention there is preferably provided, through one or more layers, parallel transverse rows of perforations whereby a tear propagates along such a row, such rows preferably extending across the strip at right angles to the edges.

Such perforations may be the interstices of a netted material constituting at least one of said layers. Suitably netted materials are those produced by melt-embossing (i.e. simultaneously profiling and solidifying a molten film of polymer) with subsequent stretching into a net of the desired degree of openness, especially when the net is not highly stretched and separated. Numerous patents and publications describe such a technique, which has been known for almost twenty years and particular reference is made to our pending applications Nos. 47403/74, 47416/74, 27636/74 and 27637/74.

Such perforations can alternatively be pierced through the material. The perforations may in this latter case be elongated slits or may be holes (i.e. possessing width as well as length). In this latter case they can be round, but are preferably rectilinear e.g. square or rhomboidal so that ready tear takes place at their corners. If rectilinear e.g. square they are preferably arranged with their sides at an angle e.g. 45° to the sides of the tape.

By suitable spacing of the rows it can be arranged that clean finger-tearability is provided at an angle to the basic transverse finger-tearability. Longitudinal finger-tearability is most generally desirable in this secondary role, but tear in other directions e.g. 30°, 45° or 60° to the transverse tear is also possible.

It is generally to be expected, however the perforations are formed, that there will be from 5 to 250 perforations per inch along each transverse row: 10 to 50 being preferred and 15 to 30 being most preferable. If slits are provided these figures may be lower according to the lengths of the slits.

Preferably the spacing of the rows is similar, and indeed a square grid pattern of perforation is valuable.

Alternatively, one or more layers may be profiled on one or both surfaces in a pattern exhibiting transverse lines of weakness, whereby a tear propagates along such a line of weakness.

The term "profiled" is intended to be understood in its broadest sense as meaning that the layer has a non-smooth outer surface having protrusions or depressions arranged so as to provide said transversely extending lines of weakness. Thus, the layer may have transversely extending rows of protrusions or depressions formed in its surface.

Preferably, the profiling is a pattern of continuous parallel grooves extending across the width of the strip, usually at 90° to the edges, but it can be continuous parallel rows of separate depressions and/or protrusions.

If it is desired to facilitate longitudinal finger-tearability, a film having on one side a set of parallel transverse grooves and on the other side a set of parallel longitudinal grooves is possible as one of the layers according to the invention. In such an instance the longitudinal grooves are preferably primary (i.e. wider than the transverse grooves). For example, the longitudinal grooves can be spaced at from 50 to 150 grooves per inch, preferably from 70 to 120 e.g. at 100 grooves per inch. The transverse grooves can be spaced at 150 to 350 grooves per inch e.g. 220 to 280 for example at 250 grooves per inch. The thickness of the film will generally be such that the grooves of the two sets of parallel grooves, located on opposite sides of the film, penetrate so that the bases of the grooves leave only a thin splittable membrane between them.

Alternatively again, one or more layers, if made of polymer as is usually the case, may be transversely oriented to provide lines of weakness, typically achieved by stretching the film by 100°-200°.

Most preferably, however, a combination of the above three expedients (perforation, profiling, orientation) is preferred, and most preferred is a combination of perforation and profiling with continuous grooves on one surface since this, in addition to facilitating transverse finger-tearability at any point, gives good air and moisture permeability and a more pleasing external appearance when the perforations are through, and the profiling is on, the back of the backing layer.

It will be apparent that while it is possible to provide transverse finger-tearability only in the covering layer, it is much preferred for the backing layer to be so provided, and is further preferred for both layers to be so provided whether in the same, similar or different fashions.

The protective layer can be a woven or non-woven or felted fabric material or can consist of a paper. It is usually provided with a release coating to permit ready detachment from the adhesive layer and may for cheapness in manufacture be identical with the backing layer. It may be of the same width as the backing layer (that is to say, the edges may be in alignment) but it is advantageous if it is somewhat wider than the backing layer since then a protruding margin is presented for gripping the protective layer and removing it.

The shape of the cover layer is an important subsidiary feature of the present invention. In a simple form it can extend as a single layer from one edge of the composite strip to the other, loosely adhered to the adhesive at either side and extending over the pad in the middle. However, it is perhaps more valuable if it is formed as two parts one extending in from one edge over the pad and the other extending in from the other edge over the pad and with the two inner edges overlapping.

The overlap can be a simple overlap or can itself be folded back to one side or the other as is customary with current first aid dressings. In this invention the overlap need not be located over the pad, and if to one side can facilitate a good grip on all layers prior to finger-tearing.

According to the present invention it is also valuable if a single layer of protective covering is provided which, over the pad, is folded back on itself as described in more detail below. This excess portion can be torn off prior to use to provide two parts of a protective layer for removal and manipulation of the dressing as is customary with the first aid dressings.

It is even possible to fold over, as the cover layer, a free margin of the backing layer, especially when the strip has longitudinal finger-tearability as well as transverse tearability.

The adhesive layer covers one surface of the backing layer. It can cover the surface in an uninterrupted fashion or it can be located thereon in a pattern of lines or dots whether randomly located or arranged in some pattern. Moreover, any pharmacologically acceptable adhesive which is capable of adhering to the skin on the application of pressure can be used. A man skilled in the art will be acquainted with the nature of suitable adhesives and with a general pattern of their application, and this feature itself does not constitute part of the present invention.

A wide range of polymeric material can be used for the backing layer or cover layer but polyolefins or polyamides are particularly valuable especially if presented as a non-homogeneous blend. For example a blend of high density polyethylene with polystyrene with polystyrene in amounts of from 70:30 to 95:5 by weight is valuable in this context.

The film used for the backing where not already perforated can optionally be somewhat stretched prior to use since this improves the finger-tearability and gives minute orifices in the film to provide air and moisture vapour transmission. Such a degree of transverse stretch can be up to 300% of the original width, but preferably it is only up to 150% for example 120%. Generally speaking longitudinal stretch is not strictly necessary but possibly a small amount e.g. up to 150% can be used to set the strip and facilitate rolling during manufacture.

The protective layer can as discussed above be generally similar in nature to the backing layer. However, slightly easier tear is often desirable and thus a similar film to that described above but possessing a surface between 50 and 150 grooves per inch (for example 100 grooves per inch on each side) is valuable.

In both the backing and the protective layer the groove shape is not critical. Usually a V-shaped groove is used but a groove with a flat base is also possible.

The invention will be further described with reference to the accompanying drawings in which:

FIG. 1 shows in perspective form a discrete first aid dressing, the component layers of which are much exaggerated in thickness for the purposes of illustration.

Figure 1:
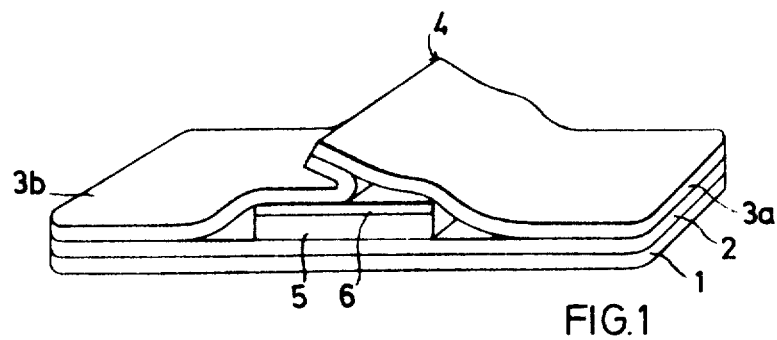
FIG. 1 shows in perspective form a prior art first aid dressing.

The first aid dressing consists of a backing layer 1, an adhesive layer 2 over the surface thereof, and a cover layer in two parts 3a and 3b attached to the adhesive layer in a removable fashion. The cover layers 3a and 3b are at their central portions overlapped as shown at 4 and cover a pad 5 adhered to the adhesive layer 2 and itself having a cover net 6.

To apply such a first aid dressing the two portions of the cover layer 3a and 3b, where they overlap at 4, are taken one in each hand between the finger and thumb, opened back to expose the absorbent pad, and used to manipulate the dressing over the pad into contact with the skin with the minimum of fingering of the dressing surface.

Figure 2A:
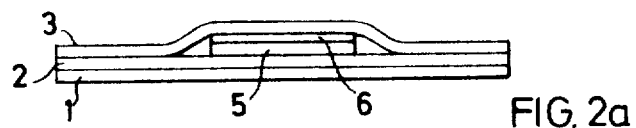
FIGS. 2a and 2b show cross-sections of composite strips according to the invention.
Figure 2B:
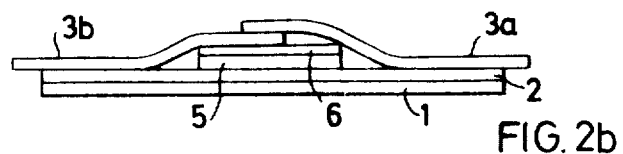

FIGS. 2a and 2b, where apposite, are labelled with the same reference numerals as the prior art of FIG. 1.

In FIG. 2a the protective cover is shown as a single leaf 3 which is peeled off from one end to the other of the dressing after this is torn from a continuous strip. In a first embodiment of the strip shown in FIG. 2a the backing layer 1 consists of a polymer blend of 85% high density polyethylene and 15% polystyrene by weight provided with longitudinal grooves packed at 100 to the transverse inch all V-shaped in cross section to leave generally similar rib members between them, the backing being provided on the other surface with generally transverse grooves at a spacing of 250 to the inch. The layer is subjected to a 160% transverse stretch to orient it. The cover layer 3 is somewhat similar except that both the longitudinal and transverse grooves are spaced at 100 to the inch. Such a material tears straight across, through the backing layer, adhesive, pad, cover and protective layer to provide a dressing of any desired width.

In an alternative embodiment of the strip of FIG. 2a, the backing layer 1 consists of a 0.004" thick film formed of an ethylene/vinyl acetate film and coated with 30 to 40 grammes per square meter of an acrylic pressure-sensitive adhesive. The layer is perforated with substantially circular holes according to a square grid pattern of 25 holes per linear inch. The cover layer 3 carries a release coating and can either be a similar perforated (or unperforated) material, or a 100—100 grooved film as above. The backing layer 1 shows good air and moisture permeability and good conformability to a non-flat surface; the dressing moreover tears equally well in a transverse or longitudinal direction once such a tear has been initiated.

The pad 5 is formed of a carboxylated butadiene-styrene latex, cross-linked with zinc oxide.

FIG. 2b shows a similar section to FIG. 2a, the only differences being that the protective layer is again shown in two portions 3a and 3b and that these portions overlap the edges of the strip 1 to provide easy gripping between finger and thumb for removal. The portions 3a and 3b are shown as having a simple overlap in the central region of the pad.

Figure 2C:
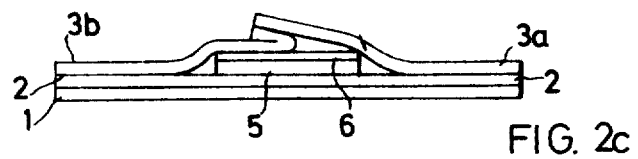

FIG. 2c shows a section through a continuous strip which is very closely analagous to the section through the discrete first aid dressings already known. The difference is of course that such dressings can be torn to any desired width from a continuous length of composite strip material by virtue of the various profiling of the component parts of the strip. The overlap portion need not be positioned over the pad; displacing it to one side allows it to be gripped readily prior to finger-tearing.

Figure 2D:
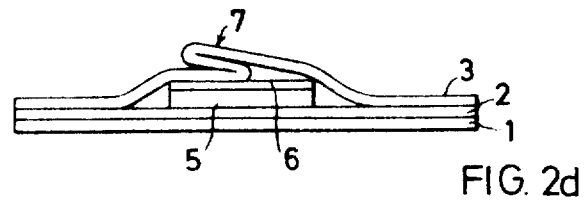

FIG. 2d shows how the same materials, profiled in the same fashion, can be used in such a way that the protective layer is folded back on itself at 7 where it overlies the pad. This particular embodiment has the advantage that the folded back portion 7 can be torn off longitudinally (in relation to the composite strip) thus leaving a structure somewhat as shown in FIG. 2c. Indeed, this can be done even more simply merely by opening out the folded over portion and simultaneously tearing the cover layer in half at this portion while peeling it back to either end of the dressing.

Figure 3:
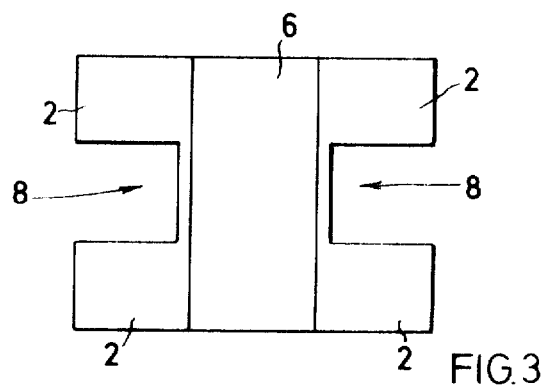
FIG. 3 shows a "butterfly" dressing which can be readily produced from the composite strip according to the invention.

FIG. 3 shows in plan form a portion of a dressing torn from a continuous strip. In this Figure, the protective cover has been removed, and the dressing exhibits its adhesive surface 2 and the pad cover 6. The square portions 8 torn out of each side enable a dressing of this shape to be applied to a digit for example, to cover a cut on the end of a finger and thus constitute a so-called "butterfly" dressing. Because of the profiling of the backing and of the protective layer the straight edges of the portions 8 can readily be obtained by tearing without the use of scissors.

Figure 4A:
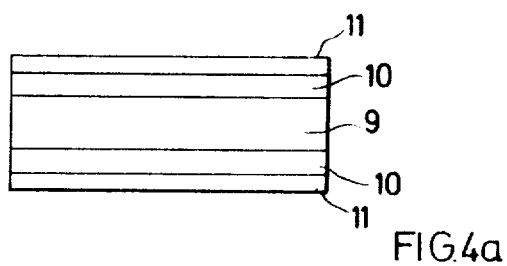
FIGS. 4a and 4b show products other than medical dressings within the scope of the invention.

FIG. 4a shows diagrammatically how a central backing layer 9 coated on each surface with adhesive 10 and provided top and bottom with a protective layer 11 can constitute the composite strip of the invention. Needless to say, the various protective layers 11 can be formulated so as to overlap e.g. as shown in FIGS. 2a and 2d. Such a double sided adhesive strip can be used for a variety of medical uses (e.g. fixing coleostomy bags) for industrial and domestic uses (e.g. attachment of advertising literature to a wall or like surface). As before, either the backing layer of the covering layers or both can be suitably profiled to give the finger-tearability properties according to the invention.

Figure 4B:
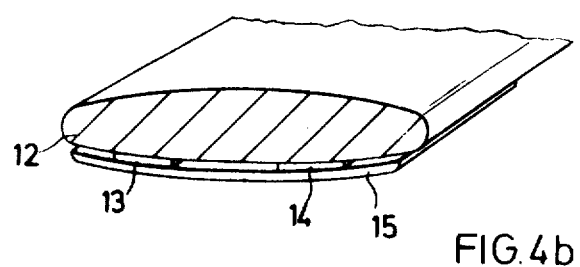

FIG. 4b shows a further form of medical product which can be formulated within the scope of the present invention. In this, the layer 12, which can be thought of as the backing layer, is bulky and fibrous and there are provided two separate strips of adhesive material at 13 and 14. The cover layer 15 extends to cover both strips and one surface of the fibrous layer. In such a case the cover layer 15 can be relatively heavy and be profiled so that its tear characteristics dominate those of the whole composite. Thus a strip of absorbent material of indeterminate length can be torn into desired sizes and, when the protective layer 15 is removed, adhered e.g. to the inner side of garments as a sanitary towel or disposable diaper pad.

We claim:

1. A composite multi-layered strip of materials tearable into individual medical dressings of any desired length comprising:
    a finger-tearable outer backing strip layer having an external surface and an internal surface;
    a finger-tearable adhesive layer disposed on said internal surface of said outer backing strip layer;
    a finger-tearable absorbent strip layer adheredly disposed on said adhesive layers, said absorbent strip layer being narrower than said outer backing strip layer so as to provide exposed margins of said adhesive layer on either side of said absorbent strip layer; and
    a finger-tearable outer protective strip layer having an external surface and an internal surface being peelably adherent to said exposed margins of said adhesive layer, each of said outer backing strip layer and said outer protective strip layer being programmed in like predetermined transverse directions to be cleanly finger tearable from any point along the length of said multi-layered strip material, one of said outer strip layers influencing transverse tear in said predetermined transverse direction of any layer adherent thereto, said outer backing strip layer influencing transverse tear in said predetermined direction of said absorbent strip layer and at least a portion of said adhesive layer serving to adhere to said absorbent strip layer whereby a joint tear in said predetermined transverse direction extending across one of said exposed margins propagates separately and coincidentally in the said outer strip layer over an unadhered portion of said outer backing strip layer with said outer protective strip layer to meet at the same point on the other of said exposed margins to continue the joint tear and to provide clearly defined separate units of any length of said composite multi-layered strip material while leaving the remaining portion of said composite multi-layered strip material with a clean transverse edge.

2. A composite strip as claimed in claim 1 wherein said absorbent strip layer is a foamed polymeric product.

3. A composite strip as claimed in claim 2 wherein said absorbent strip layer is a styrene-butadiene foam rubber layer.

4. A composite strip as claimed in claim 1 which is rendered cleanly finger-tearable in the predetermined transverse direction starting from any point along its length by parallel transverse rows of perforations passing through one or more layers of the strip, whereby a tear propagates along such a row.

5. A composite strip as claimed in claim 4 wherein said rows extend at right angles to the edges.

6. A composite strip as claimed in claim 4 in which the perforations are the interstices of a netted material constituting at least one of said layers.

7. A composite strip as claimed in claim 4 in which the perforations are pierced through the material.

8. A composite strip as claimed in claim 7, wherein the perforations are in the form of elongated transverse slits.

9. A composite strip as claimed in claim 7, in which the perforations are in the form of holes possessing width as well as length.

10. A composite strip as claimed in claim 9, in which the said holes are generally circular.

11. A composite strip as claimed in claim 9, in which the said holes are rectilinear.

12. A composite strip as claimed in claim 11, in which the said holes are square with their sides at substantially 45° to the sides of the tape.

13. A composite strip as claimed in claim 4, in which each row possesses from 5 to 250 perforations per inch.

14. A composite strip as claimed in claim 13, in which each row possesses from 10 to 250 perforations per inch.

15. A composite strip as claimed in claim 13 in which the rows are spaced at from 5 to 250 rows per inch.

16. A composite strip as claimed in claim 15, in which the rows are spaced at from 10 to 50 rows per inch.

17. A composite strip as claimed in claim 13 in which the perforations are arranged in a square grid pattern.

18. A composite strip as claimed in claim 1 which is profiled on one or both surfaces in a pattern exhibiting transverse lines of weakness whereby a tear propagates along such a line of weakness.

19. A composite strip as claimed in claim 18, wherein the profiling is constituted by a pattern of continuous parallel grooves extending across the width of the strip.

20. A composite strip as claimed in claim 19, wherein such parallel grooves are provided on each surface of at least one layer and lie in intersecting directions.

21. A composite strip as claimed in claim 20, wherein one set of grooves is transverse at 90° to the edges and the other set is longitudinal.

22. A composite strip as claimed in claim 21 wherein one set of grooves is spaced at from 50 to 150 grooves per inch.

23. A composite strip as claimed in claim 21 wherein said other set of grooves is spaced at 150 to 350 grooves per inch.

24. A composite strip as claimed in claim 18 wherein the profiling is constituted by a pattern of continuous parallel rows of protrusion and/or depressions extending across the width of the strip.

25. A composite strip as claimed in claim 1 also possessing clean finger-tearability in a predetermined longitudinal direction starting from any point across the width.

26. A composite strip as claimed in claim 25, wherein there are parallel rows of perforations and wherein the spacing between the rows is such as to confer the said longitudinal clean finger-tearability.

27. A composite strip as claimed in claim 25 in which there is a profiling of longitudinal grooves the spacing and nature of which is such as to confer longitudinal clean finger-tearability.

28. A composite strip as claimed in claim 1 in which the cover layer is of the same width as the backing layer.

29. A composite strip as claimed in claim 1 in which the cover layer is wider than the backing layer to present a protruding margin for gripping the cover layer prior to removal.

30. A composite strip as claimed in claim 28 in which the cover layer is formed as two parts one extending in from each edge with the two inner edges overlapping.

31. A composite strip as claimed in claim 30, wherein the said overlapping edges are folded back.

32. A composite strip as claimed in claim 1 wherein said absorbent strip layer has an upper cover layer of net.

33. A composite strip as claimed in claim 1 wherein the backing layer and/or the cover layer is a polymeric layer comprising of polyolefin or polyamide.

* * * * *